United States Patent [19]
Gatti et al.

[11] Patent Number: 5,719,761
[45] Date of Patent: Feb. 17, 1998

[54] CONFIGURATION CONTROL SYSTEM FOR CONFIGURING MULTIPLE BIOMEDICAL DEVICES

[75] Inventors: Joe D. Gatti; William R. Ewing, both of San Diego, Calif.

[73] Assignee: Alaris Medical Systems, Inc., San Diego, Calif.

[21] Appl. No.: 5,249

[22] Filed: Jan. 15, 1993

[51] Int. Cl.$^6$ ............................................. G05B 19/00
[52] U.S. Cl. ........................... 364/130; 364/138; 364/188; 604/67
[58] Field of Search ..................... 364/131, 132, 364/130, 184, 188, 134, 133, 138, 137, 187; 128/DIG. 13; 604/67

[56] References Cited

U.S. PATENT DOCUMENTS

| | | | |
|---|---|---|---|
| 4,304,001 | 12/1981 | Cope | 364/132 |
| 4,700,292 | 10/1987 | Campanini | 364/132 X |
| 4,752,868 | 6/1988 | Nicholas et al. | 364/191 X |
| 4,756,706 | 7/1988 | Kerns et al. | 604/66 |
| 4,898,578 | 2/1990 | Rubalcaba, Jr. | 364/188 |
| 4,958,270 | 9/1990 | McLaughlin et al. | 364/187 |
| 5,041,086 | 8/1991 | Koenig et al. | 604/65 |
| 5,100,380 | 3/1992 | Epstein et al. | 604/67 |

FOREIGN PATENT DOCUMENTS

| | | | |
|---|---|---|---|
| 0 319 218 A3 | 6/1989 | European Pat. Off. | A61M 5/14 |
| 0 490 511 A3 | 6/1992 | European Pat. Off. | G11C 16/06 |
| WO 84/00493 | 2/1984 | WIPO | A61M 5/14 |
| WO 84/00894 | 3/1984 | WIPO | A61M 5/14 |

OTHER PUBLICATIONS

Van Wolverton; "Running MS DOS"; 1989 pp. 121–123; Microsoft Press.

*Model 2001, Medfusion Syringe Infusion Pump—Operations Manual*, Medfusion, Inc., P/N 9–73–20000–0–3, Revision 3, Nov., 1991, pp. 5–10.

Primary Examiner—Reba I. Elmore
Assistant Examiner—Brian C. Oakes
Attorney, Agent, or Firm—Fulwider Patton Lee & Utecht, LLP

[57] ABSTRACT

A system for configuring a second biomedical device in the same configuration as a first device. The first device is configured as desired and then is connected through a communication link to the second device to be configured. A teach mode is invoked in the first device and a learn mode invoked in the second device. The first device receives identification data from the second device, such as the model number and software revision number. If acceptable, the first device compares individual parameters against default values. The first device then sends only those parameters which differ from the default values. The second device will then load these parameters plus the default value of the other parameters. Both devices will indicate a successful transfer of data by means of a display. If the identification data do not match, the first device will provide a prompt and no configuration data will be sent to the second device. The devices will issue a prompt if after a configuration session has occurred, the operator attempts to switch off the power to the device to exit the configuration mode or attempts to enter the teach mode without first assigning a new configuration name. Each device includes a continuously powered display for continually displaying that assigned multi-character name, even during conditions of power-off.

31 Claims, 13 Drawing Sheets

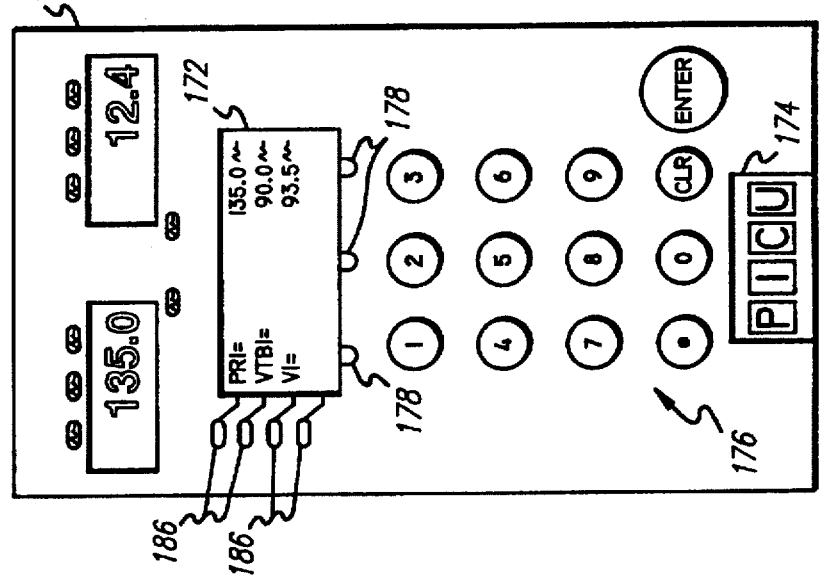

5,719,761

CONFIGURATION CONTROL SYSTEM FOR CONFIGURING MULTIPLE BIOMEDICAL DEVICES

BACKGROUND

The invention relates generally to configuring biomedical devices, and more particularly, to a system for configuring multiple biomedical devices identically.

Configuration of a single biomedical device, such as an infusion pump, may take from several minutes to an hour, or longer, to accomplish. Configuration can involve setting the maximum infusion rate, setting the air-in-line alarm threshold level, setting the maximum pressure that can be applied by the pump, and other parameters. When several to hundreds of such biomedical devices must be configured, a significant amount of time is required by skilled personnel. Typically, a biotechnical engineer on the hospital staff or available from another source individually configures each of the biomedical devices as required. This can result in substantial personnel costs to the hospital as well as a substantial down time during which the pumps are undergoing reconfiguration and are unavailable for use.

In many cases, a large number of the same type of biomedical devices must be configured identically. For example, all infusion pumps in a neonatal ward may have the identical alarm threshold levels, identical maximum infusion rates, and other operational parameters. In the case where each of the infusion devices used in the ward must be configured individually, a substantial amount of time may be required before all pumps are available for use.

An additional consideration is determining what configuration any particular biomedical device has once it has been configured. In many cases, it is not apparent what that configuration is, nor is it easily determinable. An example for an infusion pump may be the rate range. A pump configured for a neonatal rate range of from 0.1 to 99.9 ml/hr would be unsuitable for use on an adult in an emergency requiring an infusion at a rate greater than 100 ml/hr. In many cases in pumps today, the configuration of the pump is not apparent unless the pump has been switched "on." And even when switched on in some such cases, the rate range is still not discernible by the operator in the normal operating mode of the device. The rate range limits can only be known from documentation that may be accompanying the device or by a service routine to be performed by a biotechnical engineer.

Infusion pumps, as well as other devices, are often kept in reserve in a "central supply" where they can be checked out for use as required. Many devices having different configurations may be shelved together in such a supply area. It is imperative that the device checked out have the configuration desired by the operator. Additionally, in hospitals and other institutions, devices may be loaned or passed from one area of the institution to another. Not being able to rapidly and accurately determine the configuration of the device can result in a slower transfer process. The operator receiving the device may be surprised by a different user interface or, worse, by different performance characteristics which may not suit the patient's needs. Another device must then be obtained with the commensurate loss of time. The constant display of a device's configuration would assist in obtaining devices from a central supply and in the transfer of devices between different hospital areas and would alert a potential user that a device needs reconfiguration before its next use.

In some prior biomedical devices, the configuration is only visible at the time the configuration process is performed. That is, the configuration name or identifier is displayed temporarily at the time the device is configured by the biotechnical engineer but is not thereafter available. Documents must be carried with the device to determine its configuration. In some other biomedical devices, the configuration is displayed only at initial power-on of the device. It is not available when the device is in a powered-off state. In another approach, the external cases of devices are made to look different, such as, given different colors. In another approach, the devices are given different model numbers for different configurations. Disadvantages to these approaches include that the device configuration cannot be easily changed by the customer and separate devices must be obtained for different applications.

In another prior approach, certain sets of configurations are pre-installed in the device, one of which can be selected through a menu offered as part of the maintenance routine of the device. The biotechnical engineer selects one of the configurations offered and the device automatically configures itself with the parameters corresponding to that selected configuration. However, custom configurations and configuration names are not available with such an approach and the configuration name is not apparent while the device is switched off.

Hence, those concerned with use, configuration, and reconfiguration of a plurality of like biomedical devices, and particularly those concerned with such configuration aspects on devices having large numbers of configurable parameters, have recognized the need for an improved, relatively simple, economical, durable, and reliable system for more rapidly configuring such devices and for indicating the set configuration to users and potential users. The present invention fulfills these needs and others.

SUMMARY OF THE INVENTION

Briefly, and in general terms, the present invention resides in a new and improved system for configuring a second biomedical device in the same configuration as a first device. In one aspect, the first device is configured with configuration parameters as desired and then is connected through a communication link to the second device to be configured. After completing such connection, a teach mode is invoked in the first device and a learn mode invoked in the second device. Certain configuration parameters set in the first device are then communicated to the second device which receives and accepts such configuration. The second device then becomes configured identically to the first device. The second device indicates acceptance of the configuration by indicating to the first device that the configuration control process is complete. Both the first and second devices indicate by means of respective displays that the reprogramming of the configuration of the second device is complete.

In another aspect in accordance with the invention, the first device compares each of its configuration parameters to the default operational parameters of the second device and communicates only those parameters which differ. Increased speed in communications and less likelihood of error results from this feature.

Before any configuration data is communicated to the second device, the first device requires the second device to identify itself. The first device then compares the identification data received from the second device to acceptable identification data stored in the first device. If the identification data received from the second device does not agree with the identification data stored in the first device, the first device will not send configuration data to the second device but will instead provide a prompt to the operator indicating such status. In the event that the identification data of the second device is acceptable to the first device, the first device will communicate the configuration data to the second device and both devices will indicate a successful transfer of data.

In a further aspect in accordance with the invention, the configuration control system will issue a reminder prompt to the operator if the configuration of the device has been changed and the operator attempts to switch off the power to the device involved or send the new configuration to a second device without first assigning a configuration name. The operator may then assign a configuration name or may continue with the power-off operation or the teach operation in which case the prompt will be overridden and the present name assigned to this configuration. However, such a prompt will not be given in the case of a learn device which was just re-configured by a teach device.

The operator may assign a multi-character name to the configuration set in the first device, which may comprise letters or numbers or both, and which becomes a part of the configuration. The first device will communicate this configuration name to the second device and that name will become part of the configuration of the second device as well as other downloaded parameters. In accordance with this latter feature, the operator is able to configure the device with custom configurations and is able to provide custom configuration names. As a result, more configurations and configuration names are available than with past systems and users can instantly determine the configuration of each device. Each configuration control system includes a continuously powered display mounted on the device for continually displaying that assigned multi-character configuration name, even during conditions of power-off.

The above and other advantages of the present invention will become apparent from the following detailed description of preferred embodiments when taken in conjunction with the accompanying drawings of an illustrative embodiment.

BRIEF DESCRIPTION OF THE DRAWINGS

FIG. 5 is a sample front panel diagram of a device which may be used to transfer a configuration to a second device;

FIGS. 6A, 6B, and 6C demonstrate front panel displays of configuration modes;

DESCRIPTION OF THE PREFERRED EMBODIMENTS

Figure 1:
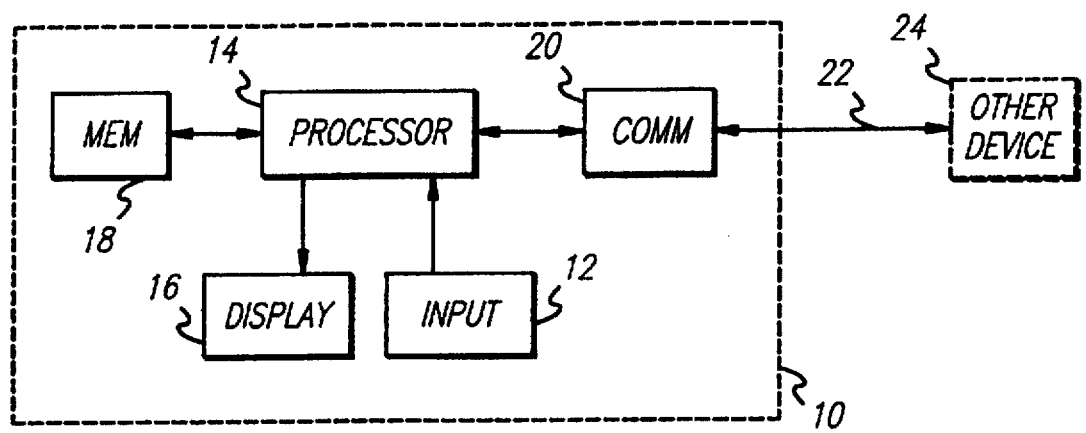
FIG. 1 is a schematic diagram of the connection of first and second devices through a communications link in accordance with one aspect of the invention.
Figure 2:
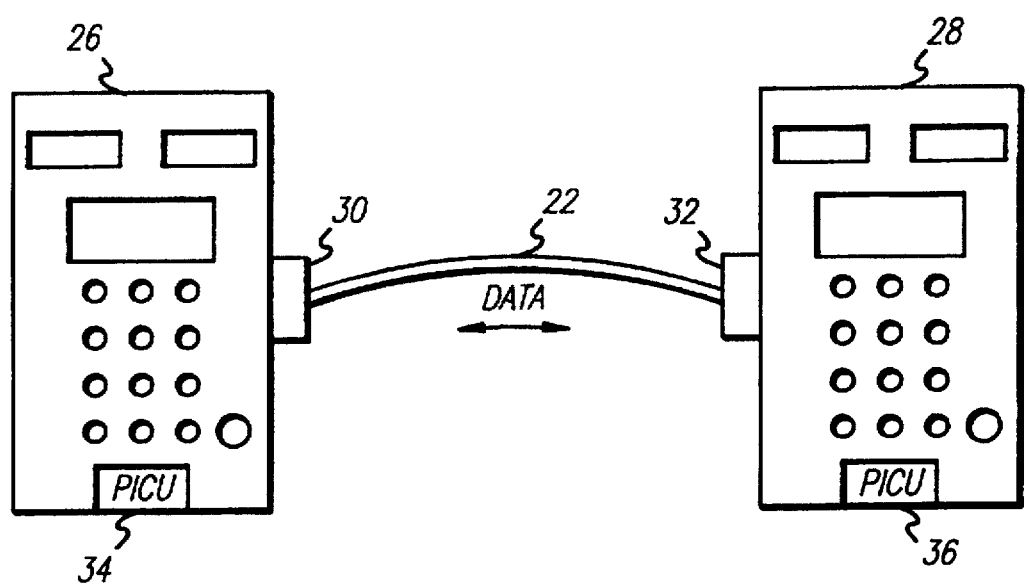
FIG. 2 is a block diagram of a system for configuring a second device in accordance with a first device.
Figure 3A:
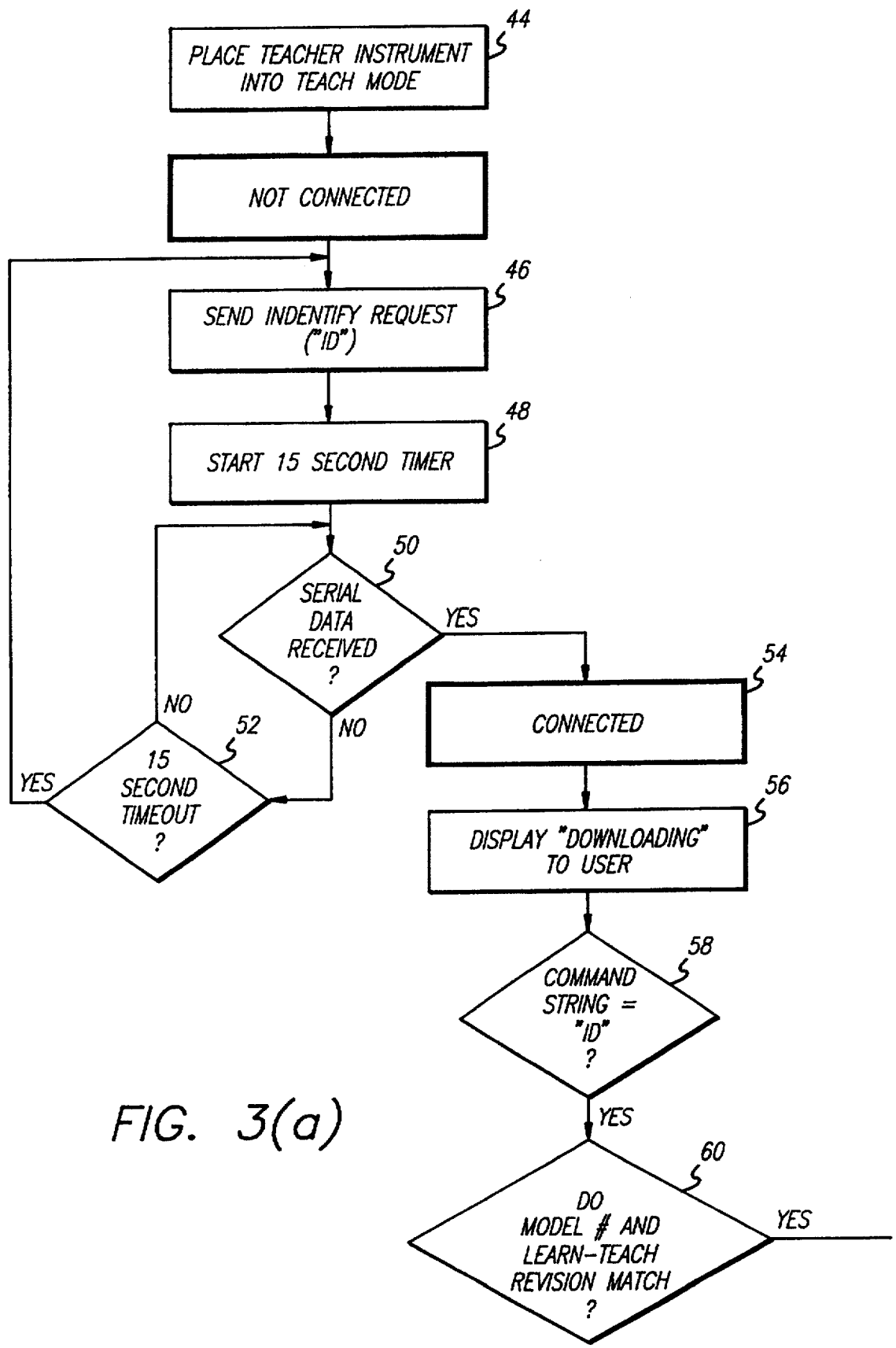
FIG. 3 is a flow chart demonstrating a method in accordance with the principles of the invention in which a first device is set into a teach mode and transfers its configuration to a second device.
Figure 3B:
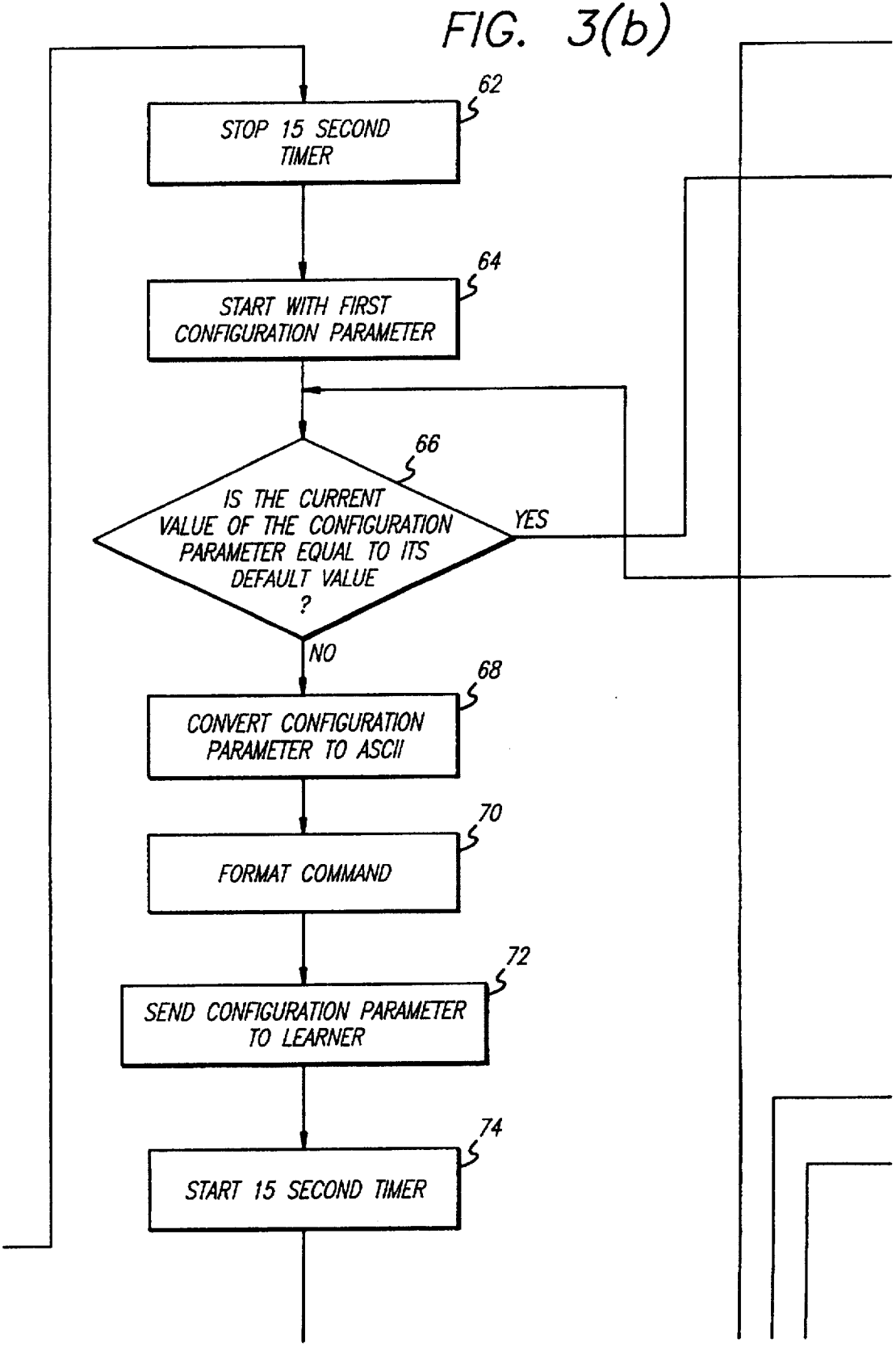
Figure 3C:
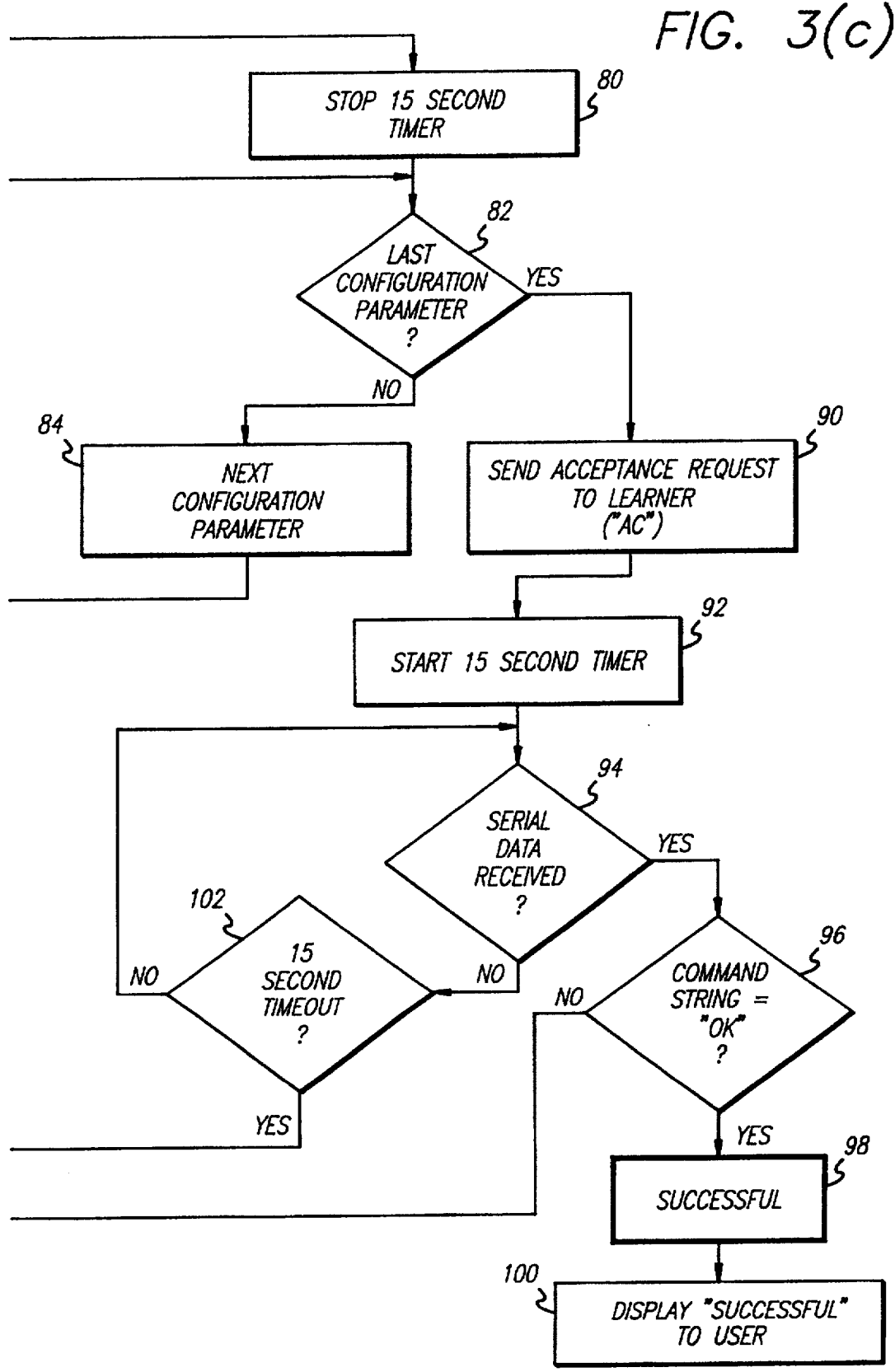
Figure 3D:
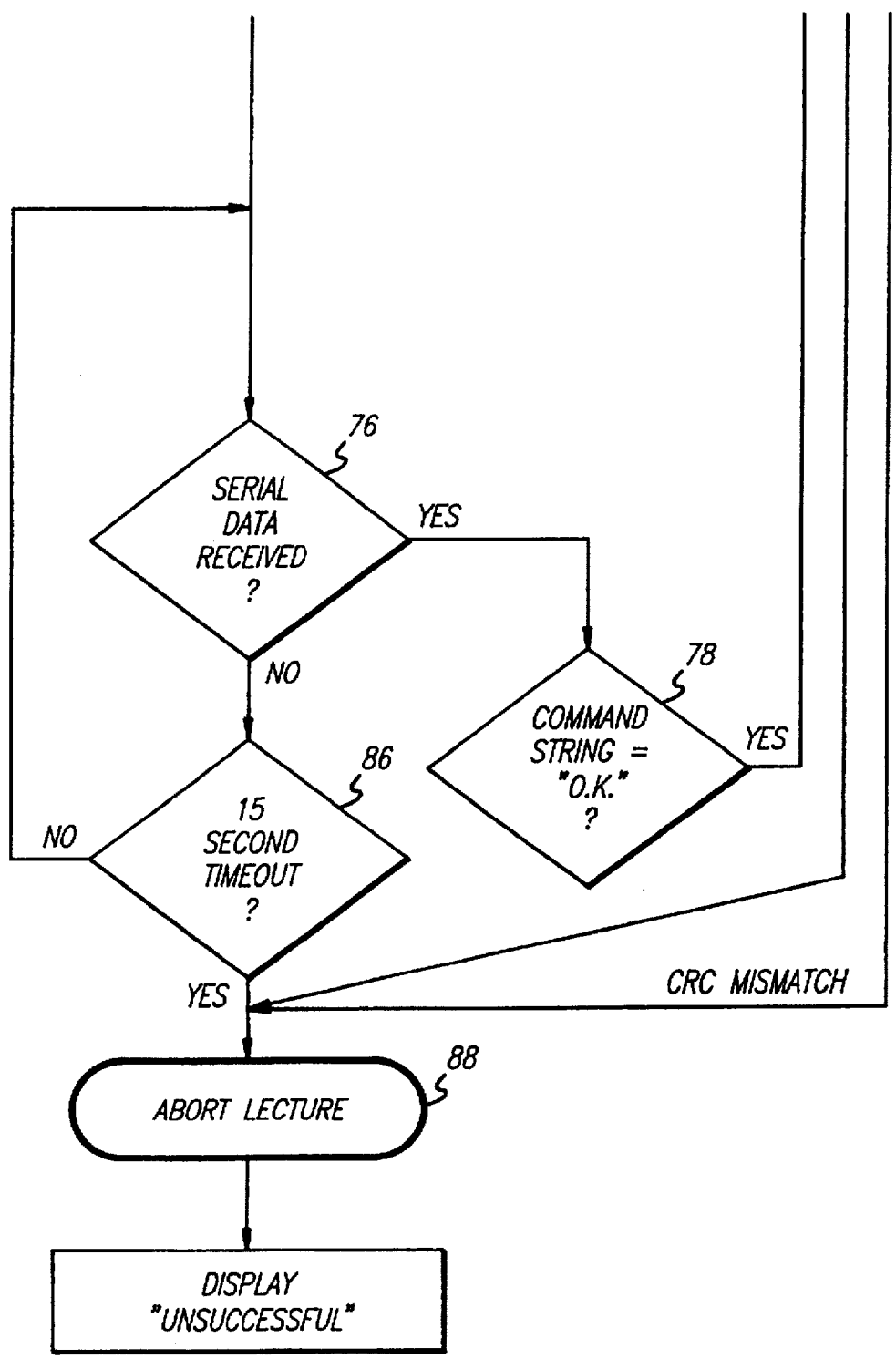
Figure 4A:
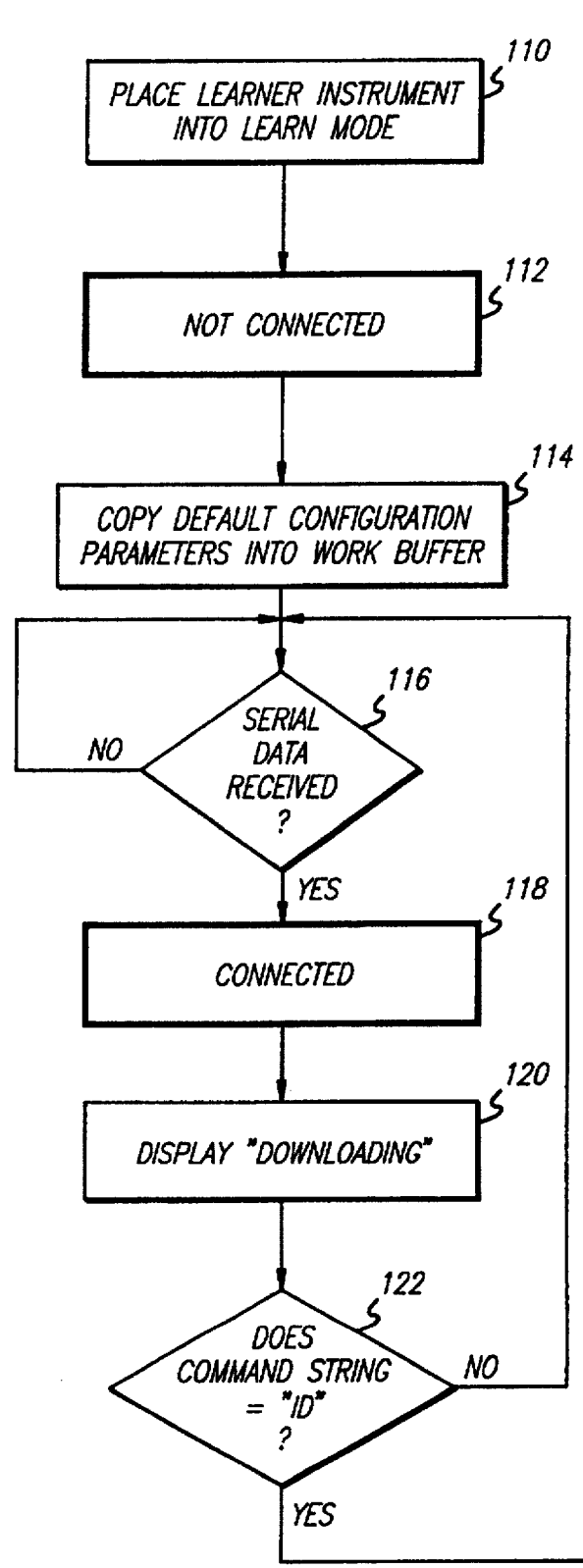
FIG. 4 is a flow chart demonstrating a method in accordance with the principles of the invention in which a second device is set into a learn mode and receives its configuration from a first device.
Figure 4B:
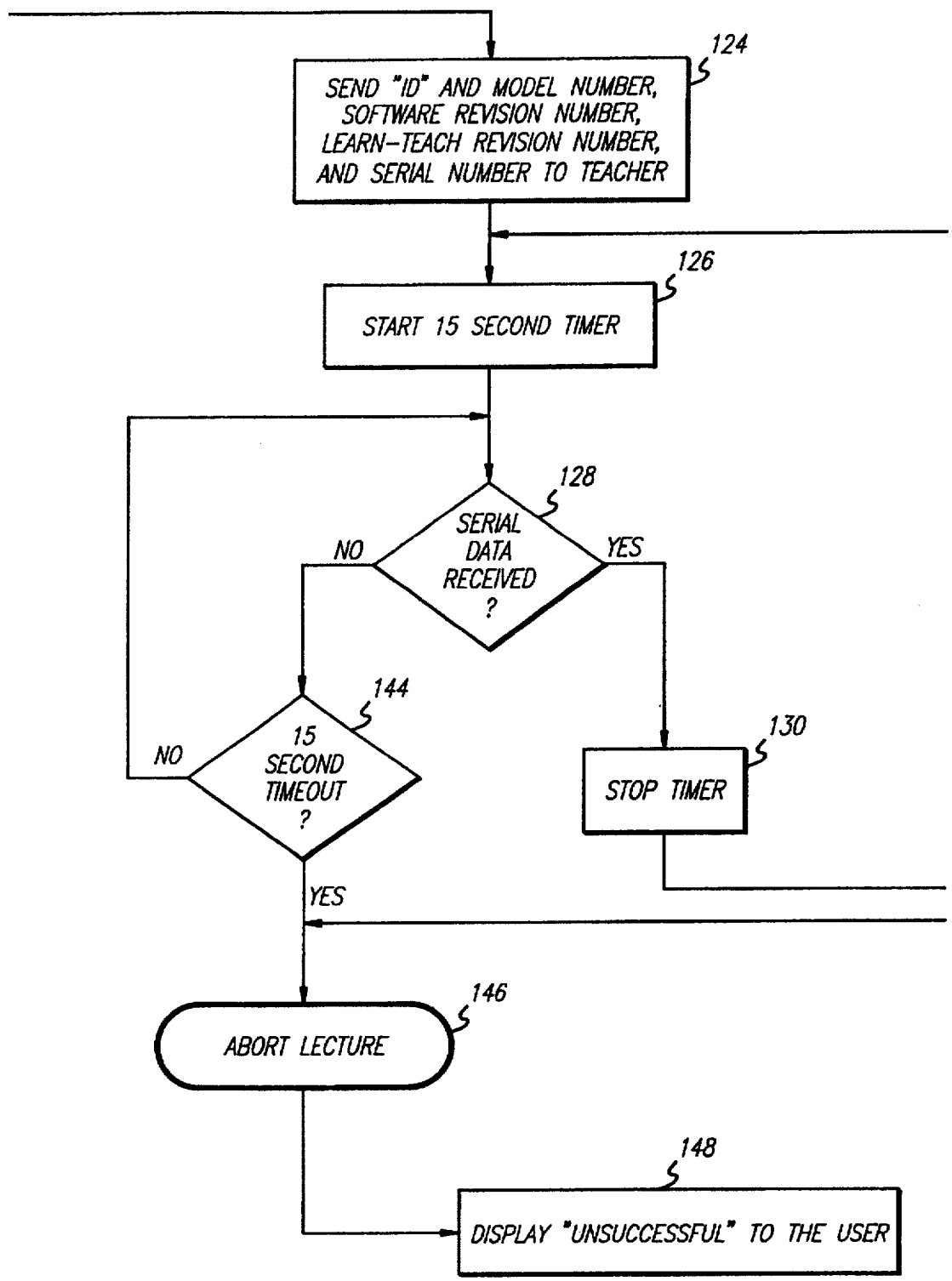
Figure 4C:
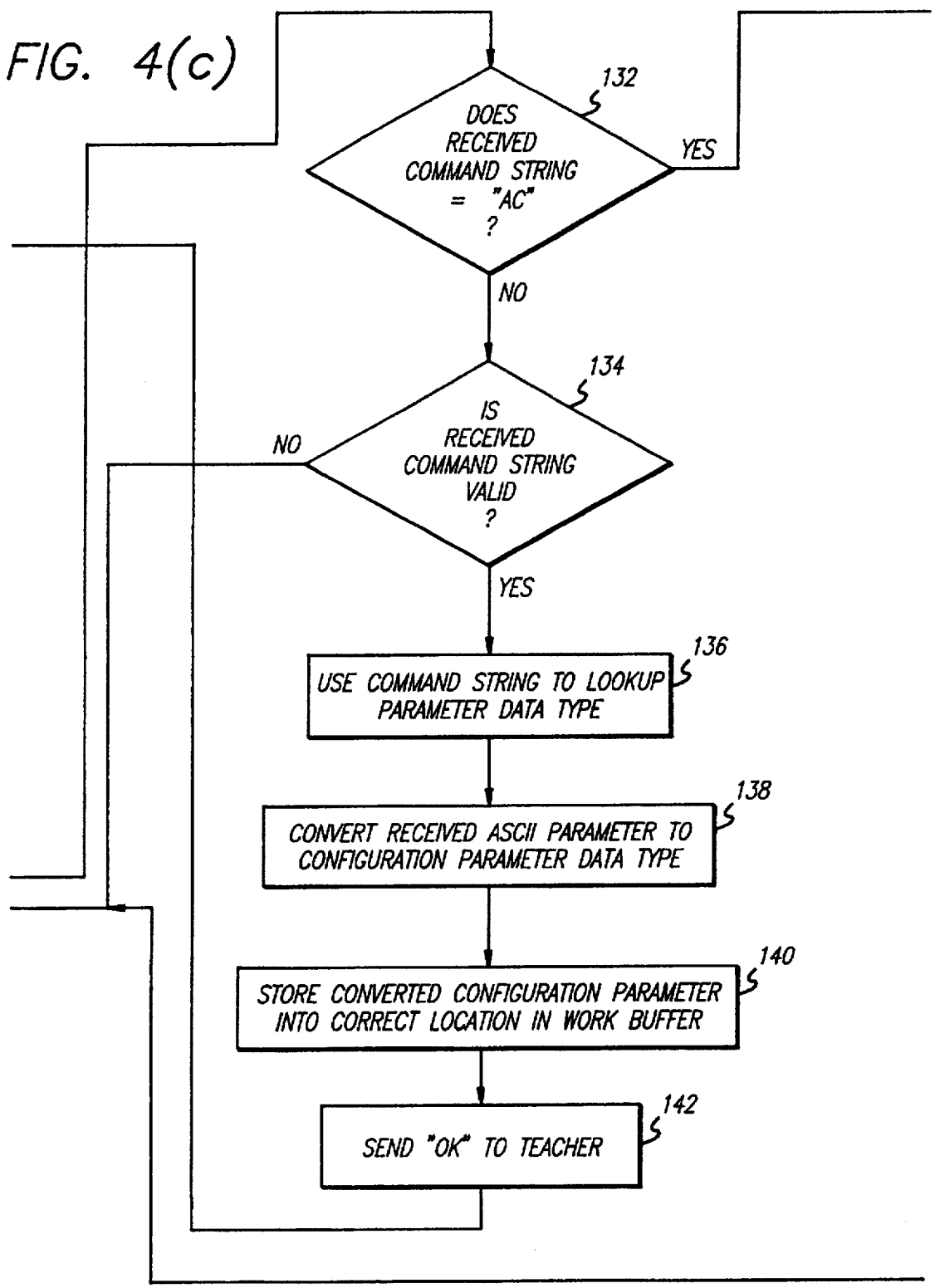
Figure 4D:
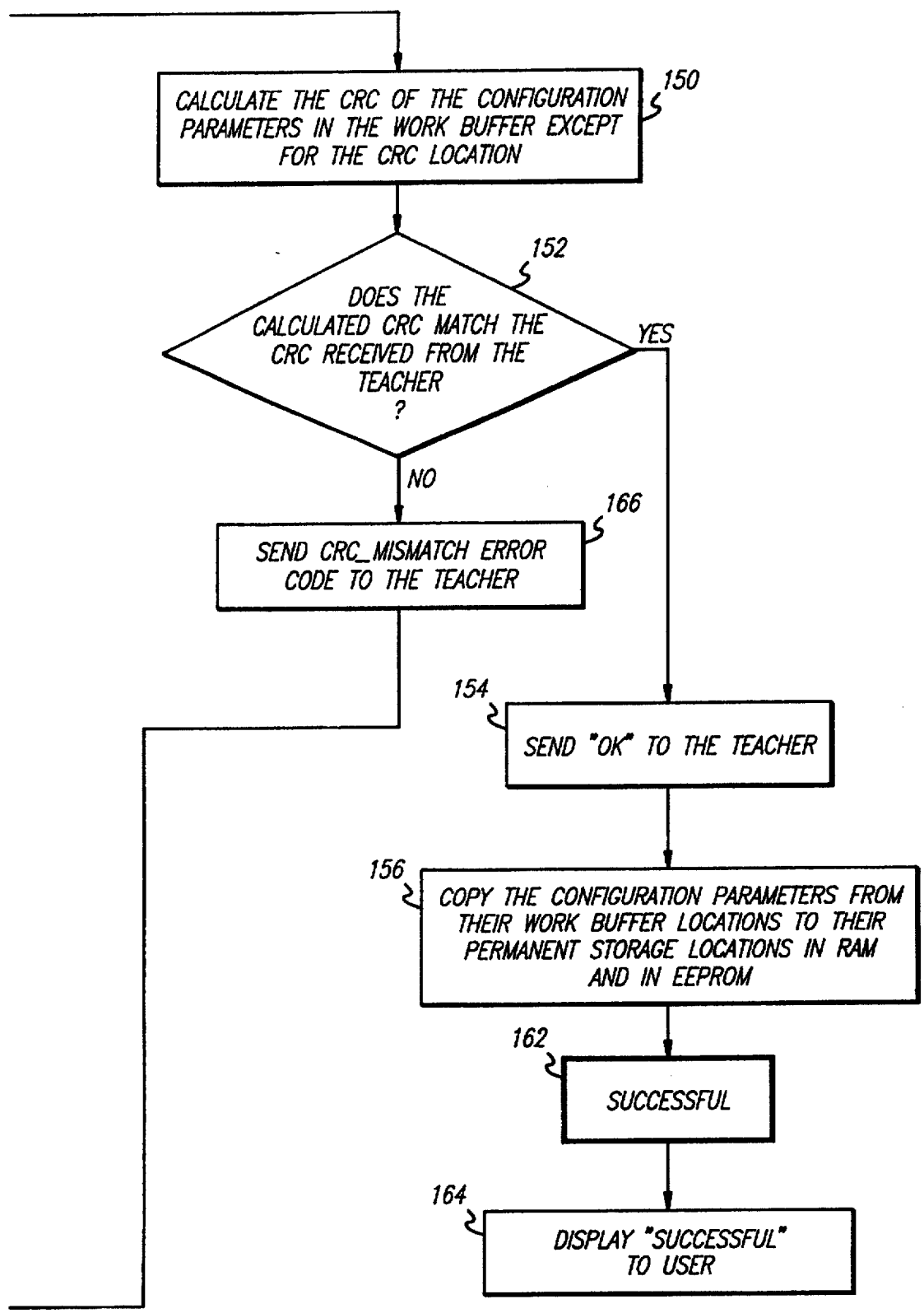

Referring now to the drawings with more particularity, wherein like reference numerals designate like or corresponding elements among the several views, there is shown in FIG. 1 a configuration control system 10 for configuring multiple biomedical devices. The control system 10 comprises in this illustration an input device 12 such as a keypad, a processor 14 which receives signals from the input device 12 and responds to them, a display 16 which presents information from the processor 14 to an operator, a memory 18 for storing data and programs, and a communications port 20 for establishing a communications link 22 with another device 24.

An application of the configuration control system discussed above is shown in FIG. 2. In this figure, a first infusion pump 26 is shown connected to a second infusion pump 28 through a communications link 22. Data is passed between them as will be described below in greater detail. The communications link in this case comprises a serial cable 22 connected between serial ports 30 and 32 of the first and second pumps respectively. The RS-232C standard is used in this embodiment. As also will be described below in more detail, each device 26 and 28 has a display 34 and 36 respectively which continuously indicates the configuration of the device, regardless of whether the device is powered or not powered. In the case of FIGS. 2, 5, 6A, 7C, 8C, and 9 the configuration name PICU (Pediatric Intensive Care Unit) is displayed.

Referring now to FIG. 3, a method embodying the principles of the invention is shown. A first device, designated the "teacher" is placed into the "teach" mode 44. The teacher then begins polling the communications link for a response from a second device. An identify request 46 is sent and a timer is started 48 which provides a fifteen-second period of time within which the teacher is to receive the identification. The teacher then waits 50 for the receipt of serial data. If no data is received within the fifteen seconds, a timeout occurs 52 and the identification request is again sent 46. In the event that serial data is received, the teacher considers itself to be connected 54 and it then displays a message indicating that data is being transferred 56. If the data received is an identification string 58, the teacher compares it to acceptable identifications 60 stored in the memory of the teacher device to verify that the second device is compatible with the teacher. The timer is then stopped 62.

The learn-teach feature is assigned its own configuration management version number, separate from the software version of the device. This allows devices which have different versions of software to transfer their configurations to one another as long as the configuration portions of the software have not been impacted by the change in software.

The teacher then starts with its first configuration parameter 64 and compares that configuration parameter to the corresponding default configuration parameter in the second device 66. In accordance with this embodiment, the teacher includes in its memory all default configuration parameters of compatible learner devices. The teacher thus compares its present configuration parameters to the default parameters stored in its memory. If the parameters are unequal, the teacher device converts the parameter data to ASCII form 68, formats a command 70, and sends the configuration parameter to the second or learner device 72. A second timer is started 74 and the teacher device waits for a correct response from the learner device 76. If a response is received indicating that the command string was acceptable 78, the timer is stopped 80 and the teacher device determines if the last parameter was sent 82. If more parameters remain, the teacher device moves to the next parameter 84 and the process is repeated.

In the case where the current configuration parameter of the teacher unit equals the default parameter value 66, the teacher device does not send the parameter to the learner device but instead proceeds to determine if this was the last configuration parameter 82, and if not, moves to the next parameter 84 as discussed above. A result of this feature is that the teacher device only sends configuration parameters which differ from those already in the learner device.

After sending a configuration parameter, the timer is monitored 86 and if the fifteen second limit is met, the configuration control process is terminated 88 and a message displayed to the operator that the process was "unsuccessful." If the time limit has not been met, the teacher continues to wait for serial data 76 and the indication that the command string was acceptable 78.

In the event that the parameter was the last parameter 82, the teacher then sends an acceptance request 90 to the learner device, and a third timer is started 92. The teacher device then waits to receive serial data 94, for the command string indicating acceptance to be received 96 and then considers the configuration control to be successful 98. A "successful" display is then provided 100 to the operator.

Once confirmed, the configuration name is displayed in a special reflective LCD display on the front panel of the device. This display along with its driver require very little drive current and are thus suitable to be kept active regardless of the power status of the device.

If the timer times out 102 before receiving the acceptance signal or if the configuration is not acceptable to the learner 96 because of CRC mismatch error, for example, the teacher then terminates the configuration control process 88. Otherwise, the teacher continues to wait for serial data 94.

Turning now to the configuration control process of the second or learner device, reference to FIG. 4 is made. The learner device is placed into a learn mode 110 and as yet is considered to be in an unconnected state 112. The default configuration of the learner device is copied into its temporary working buffer 114 and the receipt of serial data is awaited 116. Upon receipt of serial data, the learner device is considered to be in a connected mode 118 and the device displays "downloading" to the operator.

Upon receiving the command string requesting identification 122, the learner device sends an ID command response which comprises identification data, such as its model number, its software revision number, its learn/teach revision number and its serial number to the teacher device 124. A timer is started 126 and the learner device waits for the receipt of serial data 128. Upon receiving serial data, the timer is stopped 130 and the received command string is reviewed to determine if it is a request for acceptance 132. If it is not such a request, the command string is evaluated for validity 134 by comparing it to a stored table of acceptable commands and determining that it is the correct data type. The command string is then used to look up the parameter data type (for example integer, float, etc.) 136 and is converted from ASCII to the configuration parameter data type 138. The configuration parameter is then stored in the temporary buffer 140 of the learner device and an OK indication sent to the teacher device. The learner device then starts the timer 126 and waits for the receipt of the next configuration parameter 128. If a timeout 144 is encountered before serial data is received, the configuration control process is terminated 146 and a display of "unsuccessful" provided to the operator 148.

When a request for acceptance is received from the teacher device 132, the learner device calculates the cyclic redundancy check (CRC) of the configuration parameters stored in the temporary work buffer, except for the CRC location, 150 and compares the calculated number with the CRC number received from the teacher device 152. If they match, the learner device sends an OK signal to the teacher device 154 and copies the buffer-stored parameters into permanent storage locations in RAM 156 and EEPROM. The EEPROM provides a configuration backup storage means for times when power to the device is completely removed. The learner device then displays "successful" to the operator 164.

However, if the CRC codes did not match 152, the learner device would send a CRC mismatch error signal to the teacher device 166 and then terminate the configuration transfer process 146 and display "unsuccessful" 148.

The use of error detection routines in serial communications is well known to those skilled in the art. In particular, cyclic redundancy checks (CRC)) are well known and are often used. In the embodiments shown herein, a 16-bit CCITT CRC polynomial is used although others may function adequately. See J. Campbell, *C Programmer's Guide to Serial Communications*, Howard W. Sams & Company, 1987, pages. 66–68.

In one embodiment, data communications take the following ASCII form:

MA500.0 where "MA" in this case is a two character initial command string identifier for the maximum pressure limit and "500.0" is the value to be transferred. Other identifiers are usable such as "KV" for the keep-vein-open rate. Each two-character identifier is followed by data having a fixed length for each identifier. That is, the length of data following the "MA" identifier may differ from the data length following the "KV" identifier. However, the length of data following each "MA" identifier is always the same, or fixed.

Turning now to FIG. 5, in which there is shown the front panel 170 of an infusion pump to which the configuration control apparatus and method of the invention may be applied. The front panel includes a main display 172 with which the operator of the configuration control system interacts. Shown in FIG. 5, the main display 172 is presenting operational parameter data; however, as will be discussed and shown in more detail below, the display 172 is also used to configure the learner devices.

The front panel 170 also includes a continuously powered configuration display 174, which in this case, presents four characters to identify the present configuration of the infusion pump. The letters "PICU" have been selected in this case and stand for pediatric intensive care unit; however, in accordance with one aspect of the invention, the operator may select any characters to indicate the configuration of the device. Also included with the front panel is a keypad 176 for the operator's use in entering data and issuing commands. In this embodiment, the pump includes "soft" keys which are available for the operator's use in sending commands to the processor. A first set of three soft keys 178 and a second set of four soft keys 186 are shown in FIG. 5; however, more or fewer may be included with the device as needed. These keys have the function as programmed by the current mode of the processor, as will be shown in reference to the following figures.

Referring now to FIG. 6A, the main display 172 is shown and is indicating that the processor is in the configuration mode. The serial number (ID No.) of the device is presented with the software revision number (SW Rev.) and the configuration identifier. In this case, the configuration identifier comprises eight characters. The first four characters are the computed CRC and the second four are the operator-assigned configuration name. The first four characters are automatically assigned by the processor as the CRC number corresponding to that configuration. The second four operator-assigned characters are assigned to the configuration, actually becoming a part of the configuration. The second set of four characters of the identifier would be the configuration name and could be, for example, the initials of the hospital area such as PICU (discussed above), ICU (intensive care unit) or OR1 (operating room 1), or others. The use of an error detection routine such as CRC combined with a configuration name result in it being very unlikely that two instruments which have the same identifier will not have the same configuration.

A continuation of the configuration menu can be obtained from the screen of FIG. 6A by pressing the "soft" key identified as "MORE" and indicated by the bar 180. As can be seen by reference to FIG. 5, this particular bar is placed over the right-most soft key 178. FIG. 6A also presents an organization technique in which each screen is given a unique code. In the screen of FIG. 6A, the code is placed in the upper right-hand corner and is "C1." This indicates that the screen is of the "C" series (in this case "C" representing the configuration menu) and is number "1" in that series. Pressing "MORE" at the right hand arrow moves to number "2" in the menu series.

FIG. 6B presents a second screen coded "C5" which indicates the learn and teach revision numbers. In accordance with one aspect of the invention, each device will include a revision code which will be checked by the teacher device to determine if the learn and teach programs of both devices are compatible. As also shown in FIG. 6B, a bar 182 has been used to establish a soft key entitled "MORE" over the center soft key 178 shown in FIG. 5 which will move the menu to page 4 of the configuration series if pressed. Other soft keys include "LEARN" and "TEACH" which may be pressed to enter the device into the learn or teach mode respectively.

Referring now to FIG. 6C, an example of how one configuration item might be set is presented. Configuration parameters for the air-in-line features of the device are presented on the main display 172. The upper right-hand corner indicates that this is a subscreen of menu page 2 in the "C" series. Additional soft keys have been indicated along the vertical left edge of the display with two bars 184. As can be seen by reference to FIG. 5, these bars indicate the two lower soft keys 186. Pressing these soft keys 186 causes different choices to be selected on the display. For example, pressing the soft key 186 corresponding to the upper bar in FIG. 6C once will cause the number "200" to be highlighted and the number "100" to be de-emphasized. Confirming this selection can be accomplished by pressing the "confirm" soft key. This will cause 200 microliters to be the air-in-line alarm threshold volume.

In accordance with the configuration control process, a device which may be called the teacher device is manually configured to suit the particular needs of the hospital or area of a hospital or other institution. In the configuration mode of the device, items such as rate range, display language, air-in-line sensitivity, occlusion pressure limits, etc., are set as needed.

Figure 7A:
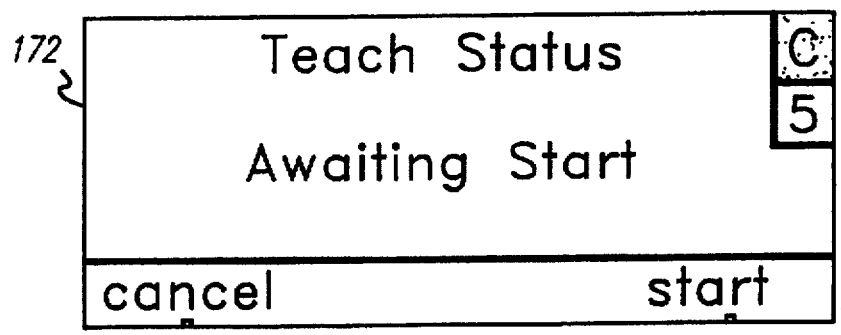
FIGS. 7A through 7D are sample displays of the teach mode of a first device.
Figure 7B:
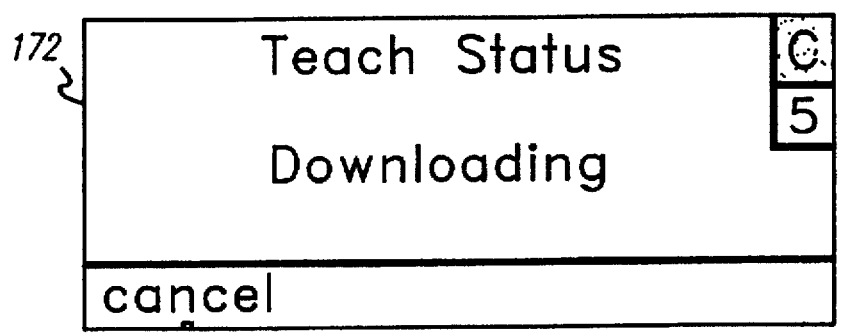
Figure 7C:
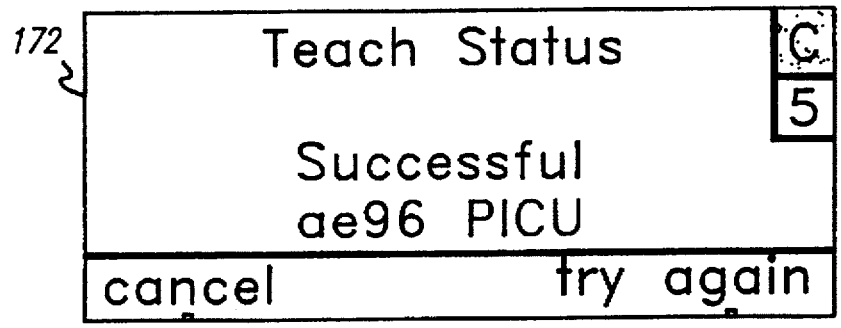
Figure 7D:
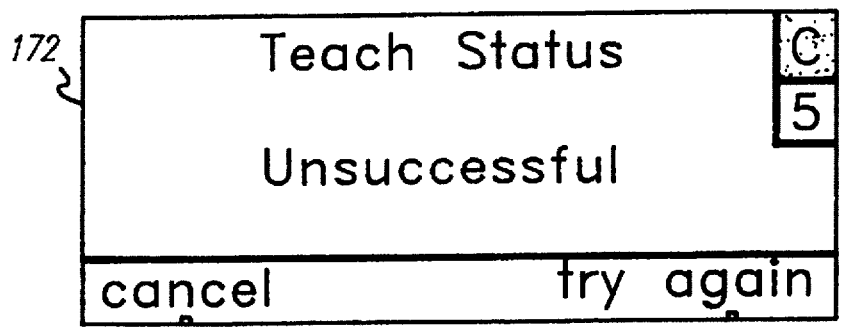

After the configuration of the teacher device has been completed, the device may now be switched into the teach mode by pressing the soft key to the left of the characters "Teach" as shown in FIG. 6B. FIG. 7A shows the device in the teach mode. The teach mode may be started by pressing the START soft key in the lower right-hand corner. In the case where the learn device has been properly connected and has the correct identification, the teach device will download parameter data and indicate this status as shown in FIG. 7B. Where all data was successfully downloaded and an identifier assigned, the teach device display will indicate this status as shown in FIG. 7C. However, where an error of some type occurred during configuration control of the learn device, the display of the teach device will indicate "unsuccessful" as shown in FIG. 7D.

As shown in FIG. 7C in the case of a successful configuration, a new learner device may be connected to the teacher device and the "try again" soft key pressed. This will repeat the above configuration process with the new device. This may be repeated until all learner devices have been configured as the teacher device.

Figure 8A:
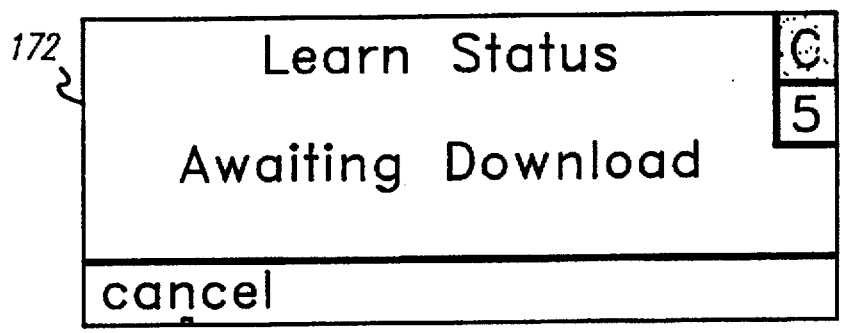
FIGS. 8A through 8D are sample displays of the learn mode of a second device.
Figure 8B:
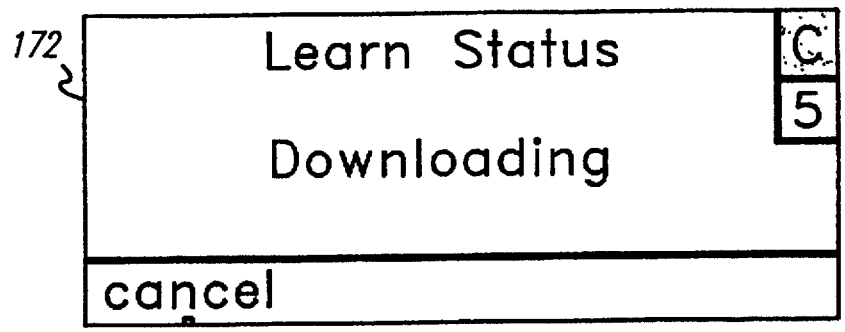
Figure 8C:
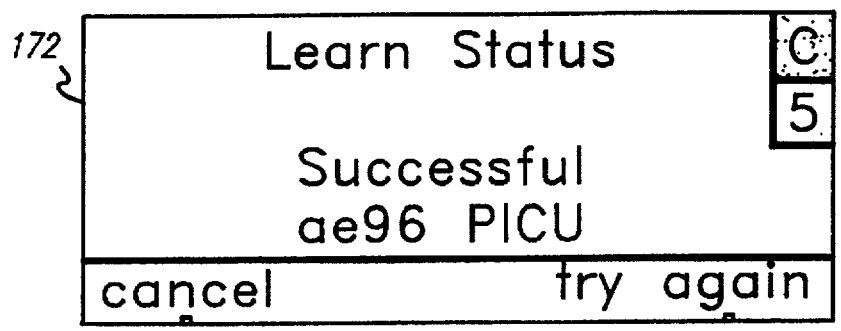
Figure 8D:
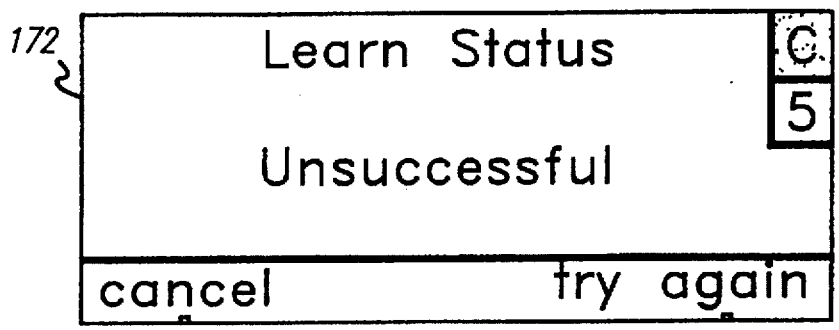

Similar screen displays are presented by the learn device during configuration control as is shown in FIGS. 8A through 8D. In FIG. 8A, the learn device has been placed into the learn mode and is awaiting the download of data from the teach device. When data is being downloaded, the display indicates such status as shown in FIG. 8B. When the configuration control was successful, i.e., all parameters were successfully transferred, a display similar to FIG. 8C is presented to the operator. However, when an error arose during data transfer or identification, a display similar to FIG. 8D is presented to the operator. Thus, displays on both devices provide real-time status of the transfer and, if successful, the second device displays the configuration name and the CRC of its new configuration.

Figure 9:
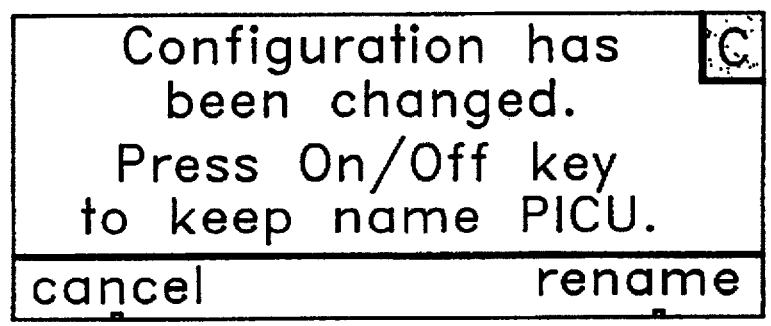
FIG. 9 is a sample display of a prompt given when a name is not assigned a new configuration.

FIG. 9 demonstrates a display presented to the operator which serves as a reminder prompt that a configuration change has been made while no configuration name change has been received by the processor. In some embodiments, an audible prompt may be given as well. This feature gives the operator a chance to rename the new configuration, or retain the same name for a new configuration. Pressing the on/off key will assign that same name (PICU in this case) to the new configuration. On the other hand, the operator may assign a new name by pressing the "rename" soft key. Without this feature, the operator may have inadvertently saved the new configuration under the PICU name thus possibly having a mix of configurations with the same name. The questioning process by this feature alerts the operator of this possibility.

It should be appreciated that the use of infusion pumps above was for illustration purposes only. The invention is not meant to be limited to infusion pumps but may have application to other devices. Additionally, instead of connecting the learn/teach devices together with a physical cable, a wireless link such as an infrared link could be used. The first device and second device could be placed next to each other and communicate with each other through the use of light-emitting and light-sensing diodes contained in each device. This would be convenient for the operator in that a cable would not have to be stored, found, and then connected between the two. Additionally, the possibility of losing the cable would not be a concern with an infrared link. A possible disadvantage is that the cost of the device may be increased due to the cost of the infrared components.

In a further improvement, parallel communications may be used rather than serial communications. Also, other types of displays for displaying the configuration name may be used as long as they do not exceed the cost and power limits of the device. The number of characters selectable for a configuration name could be increased and is constrained only by the cost of displaying them to the user. Additionally, removable storage media in the device may be programmed for proper configuration either by an accessory custom device, a personal computer or other device. Furthermore, the teach device need not be manually configured. The keypad need not be used for the initial configuration; its configuration may be set by connecting the device to a computer which then would download the configuration from a database of predetermined configurations generated off-line.

Although the invention has been described and illustrated in the context of a teacher device connecting to and teaching a single learner device, the principles of the invention may apply to the arrangement where a single teacher device is connected to a plurality of learner devices simultaneously, such as through a network. The teacher may adjust its timing and routines to wait until all learners have identified themselves and have responded to each teacher command.

The concept that a device without the help of any external or custom devices can communicate its configuration to another device of like type can provide significant time savings in configuring multiple devices and provides a significant advantage to users. The configuration control system of the present invention satisfies a long-existing need for an improved, relatively simple, economical, and reliable system for configuring multiple devices identically. Additionally, the system of the invention tends to ensure against mistaken use of inappropriately configured devices.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. Apparatus for controlling a plurality of independently programmable and independently operable devices, each device having an identical set of configuration parameters for controlling its operation, each configuration parameter having a range of user-selectable values, to have the same configuration so that the devices may operate independently of each other with the same configuration, the apparatus comprising:

a first switch included in each of the devices which when activated, provides a teach mode signal;

a second switch included in each of the devices which when activated, provides a learn mode signal;

an input device included in each of the devices that selects configuration parameters of the device;

a disconnectable communications link connected between two of the plurality of the independently operable devices that communicates configuration parameters between the two whereby the link may be disconnected from the two devices so that the devices may operate independently of each other;

a processor included in each of the devices that is responsive to the teach mode signal to provide a configuration signal representative of at least one of its user-selected configuration parameter values to the communications link and is responsive to the learn mode signal to receive configuration signals through the communications link that cause the device in the learn mode to be configured identically with the device in the teach mode, and to provide a signal through the communications link indicating that the configuration of the independently operable device is complete, and is responsive to character selection signals received from the input device to assign a configuration name to the current set of configuration parameters, and provides said configuration name to the device in the learn mode; and a display disposed on each of the plurality of devices responsive to the configuration complete signal indicating that the configuration of a device is complete.

2. Apparatus for controlling a plurality of independently programmable and independently operable biomedical devices, each biomedical device having an identical set of configuration parameters for controlling its operation, each configuration parameter having a range of user-selectable values, to have the same configuration so that the biomedical devices may operate independently of each other with the same configuration, the apparatus comprising:

a first switch included in each of the devices which when activated, provides a teach mode signal;

a second switch included in each of the devices which when activated, provides a learn mode signal;

an input device included in each of the devices that selects configuration parameters of the device;

a disconnectable communications link connected between two of the plurality of the independently operable devices that communicates configuration parameters and other data between the two whereby the link may be disconnected from the devices so that the devices may operate independently of each other with the same configuration;

a processor included in each of the biomedical devices that is responsive to the teach mode signal to provide a configuration signal representative of at least one of its user-selected configuration parameter values to the communications link and is responsive to the learn mode signal to receive configuration signals through the communications link and configure the device identically with the device in the teach mode according to those received configuration parameters and to provide a signal through the communications link indicating that said configuration of the device is complete, and is responsive to character selection signals received from the input device to assign a configuration name to the current set of configuration parameters, and provides said configuration name to the device in the learn mode; and a display included in each of the plurality of biomedical devices responsive to the configuration complete signal and indicating that the configuration of the second device is complete;

wherein the processor responding to the teach mode signal is also responsive to a predetermined identification signal received from the device in the learn mode through the communications link to select only those user-selected configuration parameter values which differ from the corresponding configuration parameter values in the device in the learn mode for downloading to the device in the learn mode through the communications link.

3. The apparatus of claim 2 wherein:

each device further comprises a memory in which is stored default configuration parameter values of the other devices of the plurality;

in response to the teach mode signal each processor compares each of its own configuration parameter values against the default configuration parameter values of another device to which it is connected stored in said memory; and the processor provides only the configuration parameter values to the other processor which differ from the stored default configuration parameter values of the other device.

4. The apparatus of claim 2 wherein:

each device further comprises a permanent memory, a non-volatile memory, and a working memory;

each processor stores the configuration parameter values received from the other processor in the working memory; and upon providing the configuration complete signal, the other processor stores the configuration parameter values from the working memory into both the permanent memory and the non-volatile memory.

5. The apparatus of claim 2 wherein each processor downloads configuration parameter values to another device over the communications link only after receiving the predetermined identification signal from the other processor.

6. The apparatus of claim 2 further comprising a memory included in each of the devices in which the respective processor stores the configuration name with the current operational parameters wherein the processor downloads the configuration name to the communications link with the downloaded parameters.

7. The apparatus of claim 6 wherein:

the configuration name comprises four alpha-numeric characters which may be selected by the operator; and further comprising a display which continuously displays the configuration name regardless of whether the first device is powered on or off.

8. The apparatus of claim 7 wherein the display comprises a four character display located on the front panel of the first device and which continuously displays the configuration name.

9. The apparatus of claim 7 wherein each of the devices:

further comprises a name detector which detects if a new configuration has been stored in the respective device;

determines if the operator has applied a new name to the current configuration;

detects if a predetermined switch has been engaged; and if so provides a prompt to the operator that a new configuration name has not yet been stored for the new configuration.

10. The apparatus of claim 9 wherein the name detector deactivates the prompt in the event that the user again engages the predetermined switch after the name prompt has been given.

11. A method for controlling a plurality of independently programmable and independently operable devices, each device having an identical set of configuration parameters for controlling its operation, each configuration parameter having a range of user-selectable values, to have the same configuration, comprising the steps of:

setting a first of said devices into a configuration mode;

configuring the first device with a plurality of user-selected values of configuration parameters;

connecting a disconnectable communications link between the first device and a second device of the plurality of devices for communicating configuration data between the two devices;

setting the first device into the teach mode in which mode a processor included in the device provides configuration parameters representative of the user-selected values of the configuration parameters of the device;

setting the second device into the learn mode in which mode the processor included in the device receives the user-selected values of the configuration parameters of the device in the teach mode to configure the device in the learn mode in accordance with those received user-selected values of the configuration parameters;

assigning a user selected configuration name to the current set of user-selected values of the configuration parameters of the device in the teach mode;

storing that assigned configuration name and associating the user-selected values of the configuration parameters with it;

transmitting configuration parameters of the first device and the configuration name to the second independently operable device over the communications link;

accepting the selected values of the configuration parameters and the configuration name of the first device received by the second device over the communications link;

configuring the second device according to those selected values of the configuration parameters received from the first device so that the second independently operable device has the same configuration and configuration name as the first independently operable device;

indicating at the first and second devices that the configuration control process was successful; and disconnecting the communications link between the first device and the second device so that the first and second devices may operate independently of each other with the same configurations.

12. The method of claim 11 wherein the step of transmitting configuration parameters of the first device comprises the step of providing only the configuration parameters to the second processor which differ from the corresponding parameters in the second device.

13. The method of claim 12 wherein the step of configuring the second device comprises storing the configuration parameters received from the first processor in a working memory in the second device; and storing the configuration parameters stored in the working memory in a permanent memory and a non-volatile memory in the second device.

14. The method of claim 11 wherein:

the step of transmitting configuration parameters comprises the step of storing in a memory default configuration parameters of the other devices;

comparing each of the first device configuration parameters against the default configuration parameters stored in said memory; and providing only the first device parameters to the second processor which differ from the stored default parameters.

15. The method of claim 11 further comprising the step of downloading first device parameter data to the second device only after receiving a predetermined identification signal from the second processor.

16. The method of claim 11 wherein the step of assigning a user selected configuration name comprises:

selecting four alpha-numeric characters to represent the current configuration;

assigning the four alpha-numeric characters as the configuration name; and continuously displaying the configuration name when power is on and off.

17. The method of claim 16 wherein the step of displaying comprises displaying the configuration name on a four character display located on the front panel of the device and continuously displaying the configuration name.

18. The method of claim 11 further comprising the steps of:
   detecting if a new configuration has been stored in the respective device;
   determining if a new configuration name has been stored which applies to the currently stored configuration;
   providing a prompt if a predetermined switch has been engaged but a new configuration name has not yet been stored for the new configuration.

19. The method of claim 18 further comprising the step of deactivating the prompt in the event that the predetermined switch is again engaged after the name prompt has been given.

20. A method for controlling a plurality of independently programmable and independently operable biomedical devices, each biomedical device having an identical set of configuration parameters for controlling its operation, each configuration parameter having a range of user-selectable values, to have the same configuration so that the devices may operate independently of each other with the same configuration, comprising the steps of:
   setting a first of said devices into a configuration mode;
   configuring the first device with a plurality of user selected values of configuration parameters;
   assigning a user-selected configuration name to the current set of selected values of the configuration parameters of the first device;
   storing that assigned configuration name and associating the selected values of the configuration parameters with the configuration name;
   connecting a communications link between the first and a second device of the plurality of biomedical devices for communicating configuration parameter values between the two devices;
   setting the first device into a teach mode in which mode a processor in the device provides configuration parameters representative of the user-selected values of the configuration parameters of the device;
   setting the second device into a learn mode in which mode the processor included in the device receives user-selected values of the configuration parameters representative of the configuration of the device in the teach mode to configure the device in the learn mode in accordance with those received configuration parameter values;
   transmitting only the first device configuration parameter values to the second device which differ from the corresponding default configuration parameter values of the second device over the communications link after receiving a predetermined identification signal from the second device;
   downloading the configuration name to the second device with the downloaded configuration parameter values;
   accepting the configuration parameter values of the first device by the second device over the communications link and configuring the second device accordingly;
   indicating at the first and second devices that the configuration control process was successful; and
   disconnecting the communications link between the first device and the second device so that the first and second devices may operate independently of each other with the same configurations.

21. The method of claim 20 further comprising the steps of:
   detecting if a new configuration has been stored in the respective device;
   determining if a new configuration name has been stored which applies to the currently stored configuration;
   providing a prompt if a power-off switch has been engaged or the step of setting the first device into the teach mode has been attempted without first storing a new configuration name for the new configuration.

22. A system for controlling a plurality of independently programmable and independently operable biomedical pumps, each pump having an identical set of configuration parameters for controlling its operation, each configuration parameter having a range of user-selectable values, to have the same configuration so that each of the pumps may operate independently of each other with the same configuration, the system comprising:
   a first switch included in each of the pumps which when activated, provides a teach mode signal;
   a second switch included in each of the pumps which when activated, provides a learn mode signal;
   an input device included in each of the pumps that selects the configuration parameters of the pump
   a disconnectable communications link connected between two of the plurality of pumps, and that communicates configuration parameters and other data between the two, whereby the link may be disconnected from the two pumps so that the pumps may operate independently of each other with the same configuration;
   a processor included in each of the biomedical pumps that is responsive to the teach mode signal to provide a configuration signal representative of at least one of its user-selected configuration parameter values to the communications link and is responsive to the learn mode signal to receive signals through the communications link that cause the biomedical pump in the learn mode to be configured identically with the pump in the teach mode, and to provide a signal through the communications link that said configuration of the biomedical pump is complete, and is responsive to character selection signals received from the input device to assign a configuration name to the current set of configuration parameters, and provides said configuration name to the device in the learn mode;
   a display disposed on each of the plurality of biomedical pumps responsive to the configuration complete signal indicating that the configuration of a biomedical pump is complete.

23. The system of claim 22 wherein:
   the biomedical pump in the teach mode is responsive to a predetermined identification signal received from the biomedical pump in the learn mode to which it is connected to provide only the configuration parameter values to the biomedical pump in the learn mode that differ from the corresponding configuration parameter values of the pump in the learn mode.

24. The system of claim 22 wherein:
   each biomedical pump further comprises a memory in which is stored a default configuration of parameter values of each of the other biomedical pumps of the plurality;
   the processor of the biomedical pump in the teach mode compares each of the configuration parameters of the pump in the teach mode against the configuration parameter values of the default configuration of a pump to which it is connected and which is in the learn mode stored in said memory in response to the teach mode signal; and the processor provides only the configuration parameter values to the other pump that differ from the stored configuration parameter values of the default configuration of the other pump.

25. The system of claim 22 wherein:

each of the pumps further comprises a permanent memory, a non-volatile memory, and a working memory;

each of the pumps stores configuration parameter values received from another pump in the working memory; and upon providing the configuration complete signal, each pump stores the configuration parameter values from the working memory into both the permanent memory and the non-volatile memory.

26. The system of claim 22 wherein the processor of each pump downloads configuration parameter values to another pump through the communications link only after receiving a predetermined identification signal from the other pump.

27. The system of claim 22 wherein each of the plurality of pumps further comprises a memory in which is stored that name with the current configuration parameter values, wherein each pump in the teach mode downloads the configuration name to each pump to which it is connected through the communications link with the downloaded configuration parameter values.

28. The system of claim 27 wherein:

the name comprises four alpha-numeric characters which may be selected by the operator; and further comprising a display which continuously displays the name regardless of whether the first biomedical pump is powered on or off.

29. The system of claim 28 wherein the display comprises a four character display located on the front panel of the first biomedical pump and which continuously displays the configuration name.

30. The system of claim 28 wherein each biomedical pump:

further comprises a name detector which detects if a new configuration has been stored in the respective biomedical pump;

determines if the operator has applied a new name to the current configuration;

detects if a predetermined switch has been engaged; and if that switch has been engaged; and provides a prompt to the operator that a new configuration name has not yet been stored for the new configuration.

31. The system of claim 30 wherein the name detector deactivates the prompt in the event that the user again engages the predetermined switch after the name prompt has been given.

* * * * *